(12) United States Patent
Kim et al.

(10) Patent No.: US 8,445,039 B2
(45) Date of Patent: May 21, 2013

(54) ANTIOXIDANT COSMETIC COMPOSITION CONTAINING EXTRACT OF PROCESSED PEONY, POLYGONATI RHIZOMA OR LILY

(75) Inventors: Dong Hyun Kim, Suwon-si (KR); Jun Seong Park, Suwon-si (KR); Jae Kyoung Lee, Seoul (KR); Hye Yoon Park, Anyang-si (KR); Soo Mi Ahn, Suwon-si (KR); Duck Hee Kim, Seoul (KR); Han Kon Kim, Suwon-si (KR)

(73) Assignee: Amorepacific Corporation, Seoul (KR)

( * ) Notice: Subject to any disclaimer, the term of this patent is extended or adjusted under 35 U.S.C. 154(b) by 75 days.

(21) Appl. No.: 13/129,957

(22) PCT Filed: Nov. 19, 2009

(86) PCT No.: PCT/KR2009/006834
§ 371 (c)(1),
(2), (4) Date: May 18, 2011

(87) PCT Pub. No.: WO2010/058982
PCT Pub. Date: May 27, 2010

(65) Prior Publication Data
US 2011/0223263 A1    Sep. 15, 2011

(30) Foreign Application Priority Data
Nov. 19, 2008    (KR) .................... 10-2008-0115368

(51) Int. Cl.
*A61K 36/00*    (2006.01)
(52) U.S. Cl.
USPC ..................... 424/773; 424/725; 424/778
(58) Field of Classification Search
None
See application file for complete search history.

(56) References Cited

U.S. PATENT DOCUMENTS
2004/0028643 A1*    2/2004    Chiba et al. .............. 424/74

FOREIGN PATENT DOCUMENTS
| CN | 1857616 A | * | 11/2006 |
| JP | 08225428 A | * | 9/1996 |
| JP | 09301883 A | * | 11/1997 |
| KR | 10-0193105 | | 6/1999 |

OTHER PUBLICATIONS

International Search Report for PCT/KR2009/006834, mailed Jun. 30, 2010.
Written Opinion of the International Searching Authority for PCT/KR2009/006834, mailed Jun. 30, 2010.
Pang, M.H. et al., The separation of the antioxidative material from the Paeoniae Radix, Hanguk Nongwhahak Hoechi, (1999), vol. 42, No. 2, pp. 170-175.
Yang, K.S. et al., Anti-lipid peroxidative effect of Extracts and its fractions *Polygonatum odoratum*, yakhak hoeji, (2002), vol. 46, No. 4, pp. 242-246.
Korean Journal of Food Science and Technology, vol. 39, No. 4, (2007), pp. 452-457.
Journal of Hebei North University (Natural Science Edition), (2008)., 06., (See abstract).

* cited by examiner

*Primary Examiner* — Chris R Tate
*Assistant Examiner* — Deborah Davis
(74) *Attorney, Agent, or Firm* — Nixon & Vanderhye P.C.

(57) ABSTRACT

The present invention relates to an antioxidant cosmetic composition, and more particularly to an antioxidant cosmetic composition containing, as an active ingredient, either an extract of at least one of peony, Polygonati rhizoma and lily, processed using a medicinal herb processing technique, or a mixture of said extract and an extract of at least one of unprocessed peony, Polygonati rhizoma and lily.

7 Claims, No Drawings

ANTIOXIDANT COSMETIC COMPOSITION CONTAINING EXTRACT OF PROCESSED PEONY, POLYGONATI RHIZOMA OR LILY

This application is the U.S. national phase of International Application No. PCT/KR2009/006834, filed 19 Nov. 2009, which designated the U.S. and claims priority to KR Application No. 10-2008-0115368, filed 19 Nov. 2008, the entire contents of each of which are hereby incorporated by reference.

TECHNICAL FIELD

The present invention relates to an antioxidant cosmetic composition, and more particularly to an antioxidant cosmetic composition containing, as an active ingredient, either an extract of at least one of peony, Polygonati rhizoma and lily, processed using a medicinal herb processing technique, or a mixture of said extract and an extract of at least one of unprocessed peony, Polygonati rhizoma and lily.

BACKGROUND ART

A medicinal herb processing technique that is a traditional Chinese medicine manufacturing technique is called "Po-je", "Hap-hwa", "Hap-yak", "Su-chi", "Po-ja", "Bub-je" and "Su-sa" in Korean. This technique can be defined as a medicine manufacturing technique of changing the inherent properties of medicinal herbs by processing the medicinal herbs on the basis of the Chinese medicine theory.

The objects of processing medicinal herbs are to clarify medicines, facilitate the storage of medicines, reduce or remove the toxicity or side effects of medicines, change the properties of medicines to make the medicines more effective, enhance the therapeutic effects of medicines, and the offensive odor and taste of medicines to facilitate the intake of the medicines.

Meanwhile, in the manufacture of cosmetic products, raw materials having various effects, including skin whitening, wrinkle reduction and skin protection, are screened and added. Among these effects, the antioxidant effect removes reactive oxygen species, which are the cause of skin aging, to retard or prevent skin aging, changes a dull and inelastic skin to a fresh and clear skin, and makes the skin to look healthy in appearance. However, only a limited number of materials are known to have the antioxidant effect, and a small number of materials which are currently being used are chemically synthesized.

Recently, various cosmetic products which employ natural materials in order to reduce skin irritation caused by various chemical substances have been developed. In addition, natural materials have reduced side effects on the skin and receive a great deal of attention from consumers. Thus, many efforts to develop natural materials useful as cosmetic raw materials are being made.

DISCLOSURE OF INVENTION

Technical Problem

Accordingly, the present inventors have conducted studies on natural materials having excellent antioxidant effects and, as a result, have found that, when a cosmetic composition is prepared using an extract of processed peony, Polygonati rhizoma or lily alone or in a mixture said extract and an extract of unprocessed peony, Polygonati rhizoma or lily, the prepared composition shows a very excellent antioxidant effect, thereby completing the present invention.

It is therefore an object of the present invention to provide a cosmetic composition having an excellent antioxidant effect.

Solution to Problem

To achieve the above object, the present invention provides an antioxidant cosmetic composition containing, as an active ingredient, an extract of at least one of processed peony, Polygonati rhizoma and lily.

The present invention provides an antioxidant cosmetic composition containing a mixture of an extract of at least one of processed peony, Polygonati rhizoma and lily and an extract of at least one of unprocessed peony, Polygonati rhizoma and lily.

Advantageous Effects of Invention

The cosmetic composition according to the present invention contains an extract of at least one of processed peony, Polygonati rhizoma and lily alone or in a mixture said extract and an extract of at least one of unprocessed peony, Polygonati rhizoma and lily, and thus has an excellent antioxidant effect of inhibiting DPPH oxidation.

BEST MODE FOR CARRYING OUT THE INVENTION

The present invention relates to an antioxidant cosmetic composition containing, as an active ingredient, an extract of at least one of processed peony, Polygonati rhizoma and lily.

The present invention also relates to an antioxidant cosmetic composition containing a mixture of an extract of at least one of processed peony, Polygonati rhizoma and lily and an extract of at least one of unprocessed peony, Polygonati rhizoma and lily. Herein, the extract of the unprocessed plant, which is mixed with the extract of the processed plant, is prepared from a plant different from a plant used to prepare the extract of the processed plant. For example, a cosmetic composition according to a preferred embodiment of the present invention may contain, as active ingredients, an extract of unprocessed peony and extracts of processed Polygonati rhizoma and lily, but the scope of the present invention is not limited thereto.

As used herein, the term "extract of the unprocessed plant" refers to an extract obtained by extracting peony, Polygonati rhizoma or lily with water or an organic solvent, which are conventionally used, without processing the plant.

Hereinafter, the present invention will be described in detail.

Peony which is used in the present invention is a perennial plant belonging to the family Ranunculaceae. It has a single flower blooming at the end of the stem. The flower is large and beautiful and is about 10 cm in diameter in cultivated forms. The flower has various colors, including red and white, and is cultivated in many horticultural varieties. The flower has about 10 petals, particularly 8-13 petals in the case of basic types. The flower petals are about 5 cm in diameter. The stamens are very numerous and yellow, and the pistils are 3-5 in number, with the stigmas turned back. The plant flowers in May to June, and in Chinese medicine, the root is used as a medicine for labor pain, abdominal pain, menstrual pain, amenorrhoea, spitting blood, anemia, bruises and like. In the present invention, in consideration of problems such as difficulty in storage (decomposition) or the quantitative decrease of effective extracts, the peony root is used in a dried form, but the scope of the present invention is not limited thereto.

Polygonati rhizoma which is used in the present invention is the dried root of *Polygonatum odoratum*, perennial plant belonging to the family Veneridae. In Chinese medicine, the plant is called "Hwang-jung", "Wi-yu" or "Ok-jook" in Korean. The stem of the plant emerges from the ground and grows to a height of about 30-80 cm. The leaves are alternate on the stem and have an acute tip and a slender edge. The plant is sweet and plain in taste and cold and nontoxic in nature. It acts mainly in the spleen, lungs, stomach and intestines, and the typical components thereof include convallamarin, convallarin, kaempferolglucoside, quercitol, vitamin A, starch and mucus.

Lily which is used in the present invention is a perennial plant belonging to the family Veneridae and grows to a height of 1 m, and the bulb looks like a slightly flattened ball. The leaves are alternate around the stem without a petiole. The flowers bloom sideward or downward in a cluster of 2-3 flowers at the end of the stem in May to June. The flowers usually have fragrance, but some varieties may also have fragrance. In the present invention, in consideration of problems such as difficulty in storage (decomposition) or the quantitative decrease of effective extracts, the lily stem (bulb) is used in a dried form, but the scope of the present invention is not limited thereto.

The cosmetic composition according to the present invention is characterized in that it contains extracts prepared by processing each of peony, Polygonati rhizoma and lily and extracting each of the processed plants with an organic solvent.

Extracts of processed peony, Polygonati rhizoma and lily can be prepared through a method comprising the steps of:

a) adding honey to peony, Polygonati rhizoma or lily and allowing the added honey to be absorbed into the plant for 30 minutes to 1 hour;

b) roasting the plant of step a) at 100-180° C. for 10 minutes to 1 hour; and c) extracting the roasted peony, Polygonati rhizoma or lily of step b) with water or an organic solvent.

The honey in step a) is added in an amount of 20-30 wt % based on the weight of peony, Polygonati rhizoma or lily used.

The extraction in step c) can be carried out according to any conventional method known in the art. For example, an extract of each of the processed peony, Polygonati rhizoma or lily can be obtained by adding water or an organic solvent to each of the processed peony, Polygonati rhizoma or lily, extracting the plant under reflux in the solvent, dipping the extract in the solvent, filtering the extract through filter cloth, centrifuging the filtered extract to separate it into the residue and the filtrate, and concentrating the separated filtrate under reduced pressure. The organic solvent which is used in the present invention can be selected from the group consisting of ethanol, methanol, butanol, ether, ethyl acetate, chloroform, and mixtures of these solvents with water. Preferably, 80% ethanol is used. Herein, the extraction temperature is preferably 10-80° C., and the extraction time is preferably 6-24 hours. If the extraction temperature and time are out of the above-specified ranges, the extraction efficiency can be reduced or the changes in the components of the extract can occur.

After the extract has been obtained using the solvent as described above, the extract may be macerated at room temperature according to a conventional method known in the art, and the macerated extract may be heated and filtered, thus obtaining a liquid-phase material. Alternatively, the extract may additionally be evaporated to remove the solvent or be spray-dried or freeze-dried.

The cosmetic composition according to the present invention contains one or a mixture of two or more selected from the extracts of the processed peony, Polygonati rhizoma and lily in an amount of 0.0001-30 wt % based on the total weight of the composition. If the content of the extract in the cosmetic composition is less than 0.0001 wt %, the antioxidant effect of the extract cannot be obtained, and if the content exceeds 30 wt %, the increase in the content will not lead to a significant increase in the effect of the extract and it will be difficult to maintain stability or prepare a formulation.

When the mixture of the extracts of the processed peony, Polygonati rhizoma and lily is used, the mixture is preferably contained in an amount of 0.0001-30 wt % based on the total weight of the composition, and each of the components of the mixture may be used in an amount suitably selected from the range of 0.0001 to 30 wt % based on total weight of the composition. Preferably, the extracts of the processed peony, Polygonati rhizoma and lily are used at a weight ratio of 1:1:1.

Also, the cosmetic composition according to the present invention may contain, in addition to the extract of at least one of the processed peony, Polygonati rhizoma and lily, an extract of at least one of unprocessed peony, Polygonati rhizoma and lily.

The extract of unprocessed peony, Polygonati rhizoma or lily is prepared by extracting peony, Polygonati rhizoma or lily with water or an organic solvent without processing the plant, and the preparation process thereof is the same as the above-described extraction process of step c). Herein, the extract of the unprocessed plant, which is mixed with the extract of the processed plant, is prepared from a plant different from a plant used to prepare the extract of the processed plant.

Furthermore, the cosmetic composition according to the present invention contains an extract of at least one of processed peony, Polygonati rhizoma and lily and an extract of at least one of unprocessed peony, Polygonati rhizoma and lily in an amount of 0.0001-30 wt % based on the total weight of the composition. If the content of the extracts in the composition is less than 0.0001 wt %, the antioxidant effect of the extract cannot be obtained, and if the content exceeds 30 wt %, the increase in the content will not lead to a significant increase in the effects of the extracts and it will be difficult to maintain stability or prepare a formulation.

When the mixture of the extract of the processed peony, Polygonati rhizoma or lily with the extract of the unprocessed peony, Polygonati rhizoma or lily is used, the mixture is preferably contained in an amount of 0.0001-30 wt % based on the total weight of the composition, and each of the components of the mixture may be used in an amount suitably selected from the range of 0.0001 to 30 wt % based on the total weight of the composition. Preferably, the extracts of the mixture are used in equal amounts.

The cosmetic composition of the present invention can be formulated as a skin lotion, an astringent lotion, a milk lotion, a nourishing cream, a massage cream, an essence, a pack, a foundation, a lipstick or a powder foundation, but the scope of the present invention is not limited thereto.

In addition, components other than the extract in the cosmetic composition can be suitably selected by a skilled in the art depending on the formulation or intended use of the cosmetic composition.

MODE FOR THE INVENTION

Hereinafter, the present invention will be described in further detail with reference to examples and test examples. It is to be understood, however, that these examples and test examples are for illustrative purposes only and are not to be construed to limit the scope of the present invention.

COMPARATIVE EXAMPLE 1

Preparation of Extract of Unprocessed Peony 1 kg of dried peony was added to 5 l of 80% ethanol aqueous solution, extracted three times under reflux, and then dipped at 15° C. for 1 day. The extract was filtered through filter cloth and centrifuged to separate it into the residue and the filtrate. The separated filtrate was concentrated under reduced pressure, thus obtaining 300 g of an extract of unprocessed peony.

COMPARATIVE EXAMPLE 2

Preparation of Extract of Unprocessed Polygonati Rhizoma 1 kg of dried Polygonati rhizoma was added to 5 l of 80% ethanol aqueous solution, extracted three times under reflux, and then dipped at 15° C. for 1 day. The extract was filtered through filter cloth and centrifuged to separate it into the residue and the filtrate. The separated filtrate was concentrated under reduced pressure, thus obtaining 230 g of an extract of unprocessed Polygonati rhizoma.

COMPARATIVE EXAMPLE 3

Preparation of Extract of Unprocessed Lily 1 kg of dried lily was added to 5 l of 80% ethanol aqueous solution, extracted three times under reflux, and then dipped at 15° C. for 1 day. The extract was filtered through filter cloth and centrifuged to separate it into the residue and the filtrate. The separated filtrate was concentrated under reduced pressure, thus obtaining 215 g of an extract of unprocessed lily.

COMPARATIVE EXAMPLE 4

Preparation of Mixture of Extracts of Unprocessed Peony, Polygonati Rhizoma and Lily 50 g of the unprocessed peony extract of Comparative Example 1, 50 g of the unprocessed Polygonati rhizoma extract of Comparative Example 2 and 50 g of the unprocessed lily extract of Comparative Example 3 were mixed with each other, dissolved completely in 800 ml of 80% ethanol aqueous solution, and then dipped at 15° C. for 1 day. Then, the mixture solution was filtered through filer cloth and centrifuged to separate it into the residue and the filtrate. The separated filtrate was concentrated under reduced pressure, thus obtaining 125 g of a mixture of extracts of unprocessed peony, Polygonati rhizoma and lily.

EXAMPLE 1

Preparation of Extract of Honey-Roasted Peony 300 g of honey was sufficiently absorbed into 1 kg of dried peony. The honeyed plant was roasted at 150° C. for 15 minutes, and then dried in the shade. The honey-roasted plant was added to 5 l of 80% ethanol aqueous solution, extracted three times under reflux, and then dipped at 15° C. for 1 day. The extract was filtered through filter cloth and centrifuged to separate it into the residue and the filtrate. The separated filtrate was concentrated under reduced pressure, thus obtaining 430 g of an extract of honey-roasted peony.

EXAMPLE 2

Preparation of Extract of Honey-Roasted Polygonati Rhizoma 300 g of honey was sufficiently absorbed into 1 kg of dried Polygonati rhizoma. The honeyed plant was roasted at 150° C. for 15 minutes, and then dried in the shade. The honey-roasted plant was added to 5 l of 80% ethanol aqueous solution, extracted three times under reflux, and then dipped at 15° C. for 1 day. The extract was filtered through filter cloth and centrifuged to separate it into the residue and the filtrate. The separated filtrate was concentrated under reduced pressure, thus obtaining 300 g of an extract of honey-roasted Polygonati rhizoma.

EXAMPLE 3

Preparation of Extract of Honey-Roasted Lily 300 g of honey was sufficiently absorbed into 1 kg of dried lily. The honeyed plant was roasted at 150° C. for 15 minutes, and then dried in the shade. The honey-roasted plant was added to 5 l of 80% ethanol aqueous solution, extracted three times under reflux, and then dipped at 15° C. for 1 day. The extract was filtered through filter cloth and centrifuged to separate it into the residue and the filtrate. The separated filtrate was concentrated under reduced pressure, thus obtaining 320 g of an extract of honey-roasted lily.

EXAMPLE 4

Preparation of Mixture of Extracts of Unprocessed Peony, Unprocessed Polygonati Rhizoma and Honey-Roasted Lily 50 g of the unprocessed peony extract of Comparative Example 1, 50 g of the unprocessed Polygonati rhizoma extract of Comparative Example 2 and 50 g of the honey-roasted lily extract of Example 3 were mixed with each other, dissolved completely in 800 ml of 80% ethanol aqueous solution, and then dipped at 15° C. for 1 day. Then, the mixture solution was filtered through filer cloth and centrifuged to separate it into the residue and the filtrate. The separated filtrate was concentrated under reduced pressure, thus obtaining 130 g of a mixture of extracts of unprocessed peony, unprocessed Polygonati rhizoma and honey-roasted lily.

EXAMPLE 5

Preparation of Mixture of Extracts of Unprocessed Peony, Honey-Roasted Polygonati Rhizoma and Unprocessed Lily 50 g of the unprocessed peony extract of Comparative Example 1, 50 g of the honey-roasted Polygonati rhizoma extract of Example 2 and 50 g of the unprocessed lily extract of Comparative Example 3 were mixed with each other, dissolved completely in 800 ml of 80% ethanol aqueous solution, and then dipped at 15° C. for 1 day. Then, the mixture solution was filtered through filer cloth and centrifuged to separate it into the residue and the filtrate. The separated filtrate was concentrated under reduced pressure, thus obtaining 135 g of a mixture of extracts of unprocessed peony, honey-roasted Polygonati rhizoma and unprocessed lily.

EXAMPLE 6

Preparation of Mixture of Extracts of Honey-Roasted Peony, Unprocessed Polygonati Rhizoma and Unprocessed Lily 50 g of the honey-roasted peony extract of Example 1, 50 g of the unprocessed Polygonati rhizoma extract of Comparative Example 2 and 50 g of the unprocessed lily extract of Comparative Example 3 were mixed with each other, dissolved completely in 800 ml of 80% ethanol aqueous solution, and then dipped at 15° C. for 1 day. Then, the mixture solution was filtered through filer cloth and centrifuged to separate it into the residue and the filtrate. The separated filtrate was concentrated under reduced pressure, thus obtaining 115 g of a mixture of extracts of honey-roasted peony, unprocessed Polygonati rhizoma and unprocessed lily.

EXAMPLE 7

Preparation of Mixture of Extracts of Honey-Roasted Peony, Honey-Roasted Polygonati Rhizoma and Unprocessed Lily 50 g of the honey-roasted peony extract of Example 1, 50 g of the honey-roasted Polygonati rhizoma extract of Example 2 and 50 g of the unprocessed lily extract of Comparative Example 3 were mixed with each other, dissolved completely in 800 ml of 80% ethanol aqueous solution, and then dipped at 15° C. for 1 day. Then, the mixture solution was filtered through filer cloth and centrifuged to separate it into the residue and the filtrate. The separated filtrate was concentrated under reduced pressure, thus obtaining 128 g of a mixture of extracts of honey-roasted peony, honey-roasted Polygonati rhizoma and unprocessed lily.

EXAMPLE 8

Preparation of Mixture of Extracts of Unprocessed Peony, Honey-Roasted Polygonati Rhizoma and Honey-Roasted Lily 50 g of the unprocessed peony extract of Comparative Example 1, 50 g of the honey-roasted Polygonati rhizoma extract of Example 2 and 50 g of the honey-roasted lily extract of Example 3 were mixed with each other, dissolved completely in 800 ml of 80% ethanol aqueous solution, and then dipped at 15° C. for 1 day. Then, the mixture solution was filtered through filer cloth and centrifuged to separate it into the residue and the filtrate. The separated filtrate was concentrated under reduced pressure, thus obtaining 114 g of a mixture of extracts of unprocessed peony, honey-roasted Polygonati rhizoma and honey-roasted lily.

EXAMPLE 9

Preparation of Mixture of Extracts of Honey-Roasted Peony, Unprocessed Polygonati Rhizoma and Honey-Roasted Lily 50 g of the honey-roasted peony extract of Example 1, 50 g of the unprocessed Polygonati rhizoma extract of Comparative Example 2 and 50 g of the honey-roasted lily extract of Example 3 were mixed with each other, dissolved completely in 800 ml of 80% ethanol aqueous solution, and then dipped at 15° C. for 1 day. Then, the mixture solution was filtered through filer cloth and centrifuged to separate it into the residue and the filtrate. The separated filtrate was concentrated under reduced pressure, thus obtaining 108 g of a mixture of extracts of honey-roasted peony, unprocessed Polygonati rhizoma and honey-roasted lily.

EXAMPLE 10

Preparation of Mixture of Extracts of Honey-Roasted Peony, Polygonati Rhizoma and Lily 50 g of the honey-roasted peony extract of Example 1, 50 g of the honey-roasted Polygonati rhizoma extract of Example 2 and 50 g of the honey-roasted lily extract of Example 3 were mixed with each other, dissolved completely in 800 ml of 80% ethanol aqueous solution, and then dipped at 15° C. for 1 day. Then, the mixture solution was filtered through filer cloth and centrifuged to separate it into the residue and the filtrate. The separated filtrate was concentrated under reduced pressure, thus obtaining 134 g of a mixture of extracts of honey-roasted peony, honey-roasted Polygonati rhizoma and honey-roasted lily.

TEST EXAMPLE 1

Test of Antioxidant Effect (DPPH Test)

To examine the antioxidant effects of the extracts and mixtures thereof prepared in Comparative Examples 1 to 4 and Examples 1 to 10, the antioxidant activities of these extracts and mixtures were evaluated by comparatively measuring the DPPH (1,1-diphenyl-2-picrylhydrazyl) DPPH oxidation inhibitory effects thereof based on the changes in absorbance caused by the reduction of the free radical DPPH (the antioxidant is oxidized). For the extracts obtained in Comparative Examples 1 to 4 and the extracts and mixtures thereof obtained in Examples 1 to 10, the decrease in absorbance caused by the inhibition of oxidation of DPPH compared to the control was measured, and the concentration at which the absorbance was 50% of the control was defined as the effective antioxidant concentration.

10 μl of each of the materials obtained in Comparative Examples 1 to 4 or Examples 1 to 10 and a positive control sample was added to 190 μl of a solution of 100 μM DPPH in ethanol to prepare a reaction solution. The reaction solution was allowed to react at 37° C. for 30 minutes, and then measured for absorbance at 540 nm. As the positive control, the widely used synthetic antioxidant Trolox was used. The results of DPPH analysis of each of the materials are shown in Table 1 below. In Table 1, $IC_{50}$ means the sample concentration at which the absorbance is reduced by 50%.

TABLE 1

| | DPPH analysis results (inhibition %) | |
|---|---|---|
| | Sample | $IC_{50}$ (ppm) |
| | Trolox | 45 |
| Comp. Ex. 1 | Extract of unprocessed peony | 76 |
| Comp. Ex. 2 | Extract of unprocessed Polygonati rhizoma | 75 |
| Comp. Ex. 3 | Extract of unprocessed lily | 80 |
| Comp. Ex. 4 | mixture of extracts of unprocessed peony, Polygonati rhizoma and lily | 95 |

TABLE 1-continued

DPPH analysis results (inhibition %)

| Sample | | IC$_{50}$ (ppm) |
|---|---|---|
| Example 1 | Extract of honey-roasted peony | 36 |
| Example 2 | Extract of honey-roasted Polygonati rhizoma | 29 |
| Example 3 | Extract of honey-roasted lily | 30 |
| Example 4 | mixture of extracts of unprocessed peony, unprocessed Polygonati rhizoma and honey-roasted lily | 56 |
| Example 5 | mixture of extracts of unprocessed peony, honey-roasted Polygonati rhizoma and unprocessed lily | 64 |
| Example 6 | mixture of extracts of honey-roasted peony, unprocessed Polygonati rhizoma and unprocessed lily | 77 |
| Example 7 | mixture of extracts of honey-roasted peony, honey-roasted Polygonati rhizoma and unprocessed lily | 49 |
| Example 8 | mixture of extracts of unprocessed peony, honey-roasted Polygonati rhizoma and honey-roasted lily | 21 |
| Example 9 | mixture of extracts of honey-roasted peony, unprocessed Polygonati rhizoma and honey-roasted lily | 60 |
| Example 10 | mixture of extracts of honey-roasted peony, Polygonati rhizoma and lily | 46 |

As can be seen in Table 1 above, the antioxidant activities of the extracts of honey-roasted plants, prepared in Examples 1 to 3, were significantly superior to those of the extracts of unprocessed plants, prepared in Comparative Examples 1 to 4. In addition, the antioxidant effects of the extracts prepared in Examples 1-3 were also significantly superior to that of the synthetic antioxidant Trolox used as the positive control.

In the case of the mixtures of the extracts of the processed plants and the extracts of the unprocessed plants, the mixture of Example 8 containing the unprocessed peony extract, the honey-roasted Polygonati rhizoma and the honey-roasted lily showed the highest antioxidant activity which was also significantly superior to that of Trolox.

FORMULATION EXAMPLE 1

Milk Lotion

A milk lotion containing a mixture of extracts of unprocessed peony, honey-roasted Polygonati rhizoma and honey-roasted lily was prepared to have the composition shown in Table 2 below (unit: wt %).

TABLE 2

| Ingredients | Content |
|---|---|
| Example 8 | 5.0 |
| Squalane | 5.0 |
| Bees Wax | 4.0 |
| Polysorbate 60 | 1.5 |
| Sorbitan sesquioleate | 1.5 |
| Liquid paraffin | 0.5 |
| Caprylic/Capric Triglyceride | 5.0 |
| Glycerin | 3.0 |
| Butylene Glycol | 3.0 |
| Propylene Glycol | 3.0 |
| Carboxyvinyl polymer | 0.1 |
| Triethanol amine | 0.2 |
| Preservative, Pigment, Perfume | Proper Amount |
| Purified water | Balance |
| Total | 100 |

FORMULATION EXAMPLE 2

Skin Lotion

A skin lotion containing a mixture of extracts of unprocessed peony, honey-roasted Polygonati rhizoma and honey-roasted lily was prepared to have the composition shown in Table 3 below (unit: wt %).

TABLE 3

| Ingredients | Content |
|---|---|
| Example 8 | 5.0 |
| Glycerin | 3.0 |
| Butylene Glycol | 2.0 |
| Propylene Glycol | 2.0 |
| Carboxyvinyl polymer | 0.1 |
| PEG 12 Nonylphenyl Ether | 0.2 |
| Polysorbate 80 | 0.4 |
| Ethanol | 10.0 |
| Triethanol amine | 0.1 |
| Preservative, Pigment, Perfume | Proper Amount |
| Purified water | Balance |
| Total | 100 |

FORMULATION EXAMPLE 3

Nourishing Cream

A nourishing cream containing a mixture of extracts of unprocessed peony, honey-roasted Polygonati rhizoma and honey-roasted lily was prepared to have the composition shown in Table 4 below (unit: wt %).

TABLE 4

| Ingredients | Content |
|---|---|
| Example 8 | 5.0 |
| Polysorbate 60 | 1.5 |
| Sorbitan sesquioleate | 0.5 |
| PEG60 hydrogenated castor oil | 2.0 |
| Liquid paraffin | 10.0 |
| Squalane | 5.0 |
| Caprylic/Capric Triglyceride | 5.0 |
| Glycerin | 5.0 |
| Butylene Glycol | 3.0 |
| Propylene Glycol | 3.0 |
| Triethanol amine | 0.2 |
| Preservative, Pigment, Perfume | Proper Amount |
| Purified water | Balance |
| Total | 100 |

FORMULATION EXAMPLE 4

Massage Cream

A massage cream containing a mixture of extracts of unprocessed peony, honey-roasted Polygonati rhizoma and honey-roasted lily was prepared to have the composition shown in Table 5 below (unit: wt %).

TABLE 5

| Ingredients | Content |
|---|---|
| Example 8 | 5.0 |
| Bees Wax | 10.0 |

TABLE 5-continued

| Ingredients | Content |
| --- | --- |
| Polysorbate 60 | 1.5 |
| Sorbitan sesquioleate | 0.8 |
| PEG60 hydrogenated castor oil | 2.0 |
| Liquid paraffin | 40.0 |
| Squalane | 5.0 |
| Caprylic/Capric Triglyceride | 4.0 |
| Glycerin | 5.0 |
| Butylene Glycol | 3.0 |
| Propylene Glycol | 3.0 |
| Triethanol amine | 0.2 |
| Preservative, Pigment, Perfume | Proper Amount |
| Purified water | Balance |
| Total | 100 |

FORMULATION EXAMPLE 5

Pack

A pack containing a mixture of extracts of unprocessed peony, honey-roasted Polygonati rhizoma and honey-roasted lily was prepared to have the composition shown in Table 6 below (unit: wt %).

TABLE 6

| Ingredients | Content |
| --- | --- |
| Example 8 | 5.0 |
| Polyvinyl Acohol | 13.0 |
| Sodium Carboxymethyl Cellulose | 0.2 |
| Glycerin | 5.0 |
| Allantoin | 0.1 |
| Ethanol | 6.0 |
| PEG 12 Nonylphenyl Ether | 0.3 |
| Polysorbate 60 | 0.3 |
| Preservative, Pigment, Perfume | Proper Amount |
| Purified water | Balance |
| Total | 100 |

The invention claimed is:

1. An antioxidant cosmetic composition which contains, as an active ingredient, an extract obtained from at least one honey-roasted plant, wherein the plant is selected from the group consisting of peony, Polygonati rhizome, and lily, and wherein the extract is prepared by a method comprising the steps of:
   a) adding honey to the plant and allowing the added honey to be absorbed into the plant for 30 minutes to 1 hour;
   b) roasting the honey-absorbed plant of step a) at 100-180° C. for 10 minutes to 1 hour to obtain a honey-roasted plant;
   c) extracting the honey-roasted plant of step b) with an aqueous or an organic solvent; and
   d) recovering the aqueous or organic solvent extract.

2. The antioxidant cosmetic composition of claim 1, wherein the composition further contains a non-honey-roasted plant extract obtained from a plant selected from the group consisting of peony, Polygonati rhizome; wherein the non-honey-roasted plant extract is obtained from a plant different from the plant used to prepare the honey-roasted plant extract; and wherein the non-honey-roasted plant extract is obtained by extracting the plant with an aqueous or an organic solvent.

3. The antioxidant cosmetic composition of claim 2, wherein the composition contains, as an active ingredient, a mixture of the honey-roasted plant extract, and a combination of the non-honey-roasted Polygonati rhizoma extract and the non-honey-roasted lily extract.

4. The antioxidant cosmetic composition of claim 1, wherein the organic solvent is at least one selected from the group consisting of ethanol, methanol, butanol, ether, ethyl acetate, chloroform, and aqueous mixtures thereof.

5. The antioxidant cosmetic composition of claim 1, wherein the honey-roasted plant extract is present in an amount of 0.0001-30 wt % based on the total weight of the composition.

6. The antioxidant cosmetic composition of claim 2, wherein the combination of the honey-roasted plant extract and the non-honey-roasted plant extract is present in an amount of 0.0001-30 wt % based on the total weight of the composition.

7. A method for preparing an antioxidant extract composition obtained from at least one plant selected from the group consisting of peony, Polygonati rhizome, and lily comprising the steps of:
   a) adding honey to the plant and allowing the added honey to be absorbed into the plant for 30 minutes to 1 hour;
   b) roasting the honey-absorbed plant of step a) at 100-180° C. for 10 minutes to 1 hour to obtain a honey-roasted plant;
   c) extracting the honey-roasted plant of step b) with an aqueous or an organic solvent; and
   d) recovering the aqueous or organic solvent extract.

* * * * *